United States Patent [19]

Foster

[11] Patent Number: 6,113,950
[45] Date of Patent: Sep. 5, 2000

[54] PROCESS FOR COATING BIOLOGICAL PESTICIDES AND COMPOSITIONS THEREFROM

[75] Inventor: James Perry Foster, Avondale, Pa.

[73] Assignee: E. I. du Pont de Nemours and Company, Wilmington, Del.

[21] Appl. No.: 09/284,003

[22] PCT Filed: Sep. 29, 1997

[86] PCT No.: PCT/US97/17393

§ 371 Date: Apr. 5, 1999

§ 102(e) Date: Apr. 5, 1999

[87] PCT Pub. No.: WO98/15183

PCT Pub. Date: Apr. 16, 1998

Related U.S. Application Data

[60] Provisional application No. 60/027,512, Oct. 7, 1996.

[51] Int. Cl.$^7$ ............... A01N 59/16; A01N 25/00; A01N 63/00; C07H 21/00; C12N 7/00
[52] U.S. Cl. ............... 424/617; 424/93.1; 424/93.2; 424/93.6; 424/405; 424/407; 424/409; 424/417; 424/489; 424/490; 424/DIG. 8; 435/235.1; 514/951; 514/972; 536/23.72
[58] Field of Search ............... 8/648; 424/93.1, 424/93.6, 617, DIG. 8, 405, 409, 417, 489, 490, 407, 93.2, 93.21, 691; 514/769, 762, 975, 772, 972, 951; 435/235.1; 536/23.71, 23.72

[56] References Cited

U.S. PATENT DOCUMENTS

| | | | |
|---|---|---|---|
| 4,094,969 | 6/1978 | Batzer et al. | 424/78 |
| 4,115,144 | 9/1978 | Chambers et al. | 106/300 |
| 4,125,412 | 11/1978 | West | 106/300 |
| 4,844,898 | 7/1989 | Komori et al. | 424/150 |
| 4,948,586 | 8/1990 | Bohm et al. | 424/406 |
| 5,124,149 | 6/1992 | Shapiro et al. | 424/93.6 |
| 5,851,545 | 12/1998 | Fowler et al. | 424/405 |

FOREIGN PATENT DOCUMENTS

| | | |
|---|---|---|
| 0 573 150 A2 | 12/1993 | European Pat. Off. . |
| 0 653 158 A1 | 5/1995 | European Pat. Off. . |
| 0 654 509 A1 | 5/1995 | European Pat. Off. . |
| 0 697 170 A1 | 2/1996 | European Pat. Off. . |
| 0 761 096 A1 | 3/1997 | European Pat. Off. . |
| 2-157204 | 6/1990 | Japan . |
| 2 043 448 | 10/1980 | United Kingdom . |
| WO 95/33378 | 12/1995 | WIPO . |
| WO 96/03041 | 2/1996 | WIPO . |

OTHER PUBLICATIONS

Bull, D.L. et al., Improved Formulations of the Heliothis Nuclear Polyhedrosis Virus, *Journal of Economic Entomology*, 69, No. 6, 731–736, Dec. 1976.

Watts, Richard J. et al., Photocatalytic Inactivation Of Coliform Bacteria And Viruses In Secondary Wastewater Effluent, *Water Research*, 29, No. 1, 95–100, 1995.

*Primary Examiner*—John Pak
*Assistant Examiner*—Frank Choi

[57] ABSTRACT

A pesticidal composition comprising particles of biological pesticides and particles of durable $TiO_2$ in an amount sufficient to substantially coat the particles of biological pesticides and process for the preparation thereof are disclosed.

8 Claims, 1 Drawing Sheet

PROCESS FOR COATING BIOLOGICAL PESTICIDES AND COMPOSITIONS THEREFROM

CROSS REFERENCE TO RELATED APPLICATIONS

This application was filed under 35 U.S.C. 371 from PCT/US97/17393, internationally filed on Sep. 29,1997, which claims priority from U.S. provisional application No. 60/027,512, filed Oct. 7, 1996.

FIELD OF THE INVENTION

The present invention relates to biological pesticide compositions comprising particles of biological pesticides coated with durable $TiO_2$ and advantageous processes useful for preparing them.

BACKGROUND OF THE INVENTION

One aspect of the present invention relates to baculoviruses which are known to have insecticidal activity. Their commercial utility has been limited though because, without special formulation, they are readily deactivated by the UV radiation in sunlight. The incorporation of UV protectants in a variety of ways is known and some can enhance the stability of these viruses somewhat, however such compositions can be complicated, expensive to prepare and further improvements in stability and compatibility with the virus are needed.

One method of stabilizing the virus is to mix a water soluble UV absorbing substance with the virus in a spray tank. One such material is a sulfonated copolymer of catechin and leucocyanidin (U.S. Pat. No. 4,094,969). Although some degree of stabilization is achieved, there is no bond between the virus and the protecting substance hence rainfall or dew may readily separate them. Most simple tank mixes of ingredients suffer from this general problem and do not offer sufficient crop protection due to the lack of UV stability of these viruses.

Microencapsulation using a variety of techniques is another method used. However these systems are limited due to the virus's sensitivity to many encapsulating precursors and the overall expense of the preparations. Many, owing to their transparency in the UV-A and -B region of sunshine, require an additional light screening agent. Typically the screening agent is incorporated into the capsule wall such as in U.S. Pat. Nos. 4,844,896 and 4,948,586; EP 0 653 158 A1; and WO 96/03041. A major problem with these preparations is the lack of a suitable triggered release matrix. In other words, the encapsulated virus is constrained in a matrix which requires some process to occur for it to be released at the site of action. These release processes typically include hydrolysis, desorption or dispersion and by their nature take time to occur. Due to the limited residence time of the virus in the insect's midgut, the site of infection, fast and complete release is necessary to reach the full infective potential of the virus The use of mineral UV screens has also been described Most do not absorb UV light but rather function by reflecting and refracting UV light. Major exceptions to this generalization are zinc oxide and titanium dioxide which have strong UV absorption bands. Although titanium dioxide ($TiO_2$) is claimed in Japan [WPI Acc. #90-228659/30, *J Econ. Entomol.* 69, 731(1976), and UK Patent Appl 2,043,4481] to enhance virus stability toward UV radiation, it is also known that when exposed to ultraviolet light from sunlight it becomes reactive. For example, a sunlight irradiated aqueous suspension $TiO_2$ produced hydroxyl radicals which inactivated viruses in waste water treatment [*Water Research* 29 (1) 95, 1995].

It has been found that a modified form of $TiO_2$, referred to as durable $TiO_2$ (as illustrated in U.S. Pat. No. 4,125,412, EP 0 654 509 Al), provides a better and easier means of stabilization of baculoviruses than known stabilizers. In addition, other advantages of the use of durable $TiO_2$ will become apparent hereinafter.

SUMMARY OF THE INVENTION

The present invention pertains to a pesticidal composition comprising particles of biological pesticides and particles of durable $TiO_2$, a modified form of $TiO_2$, in an amount sufficient to substantially coat the particles of such biological pesticides; and an advantageous process for the preparation thereof. More specifically, the present composition pertains to an insecticidal baculovirus with an improved stabilizer.

The durable $TiO_2$ can be simply mixed with a biological pesticide, preferably though, durable $TiO_2$ is substantially coated on the surface of the biological pesticide. According to one preferred embodiment of the present invention, addition of an aqueous slurry of durable $TiO_2$ to a stirred aqueous slurry of a baculovirus at neutral pH (or alternately the virus to the $TiO_2$ slurry) causes the durable $TiO_2$ and the baculovirus to co-precipitate. Preferably, this material is then spray dried to particles less than 50 micron median volume diameter (mvd).

DETAILED DESCRIPTION OF THE INVENTION

Figure 1:
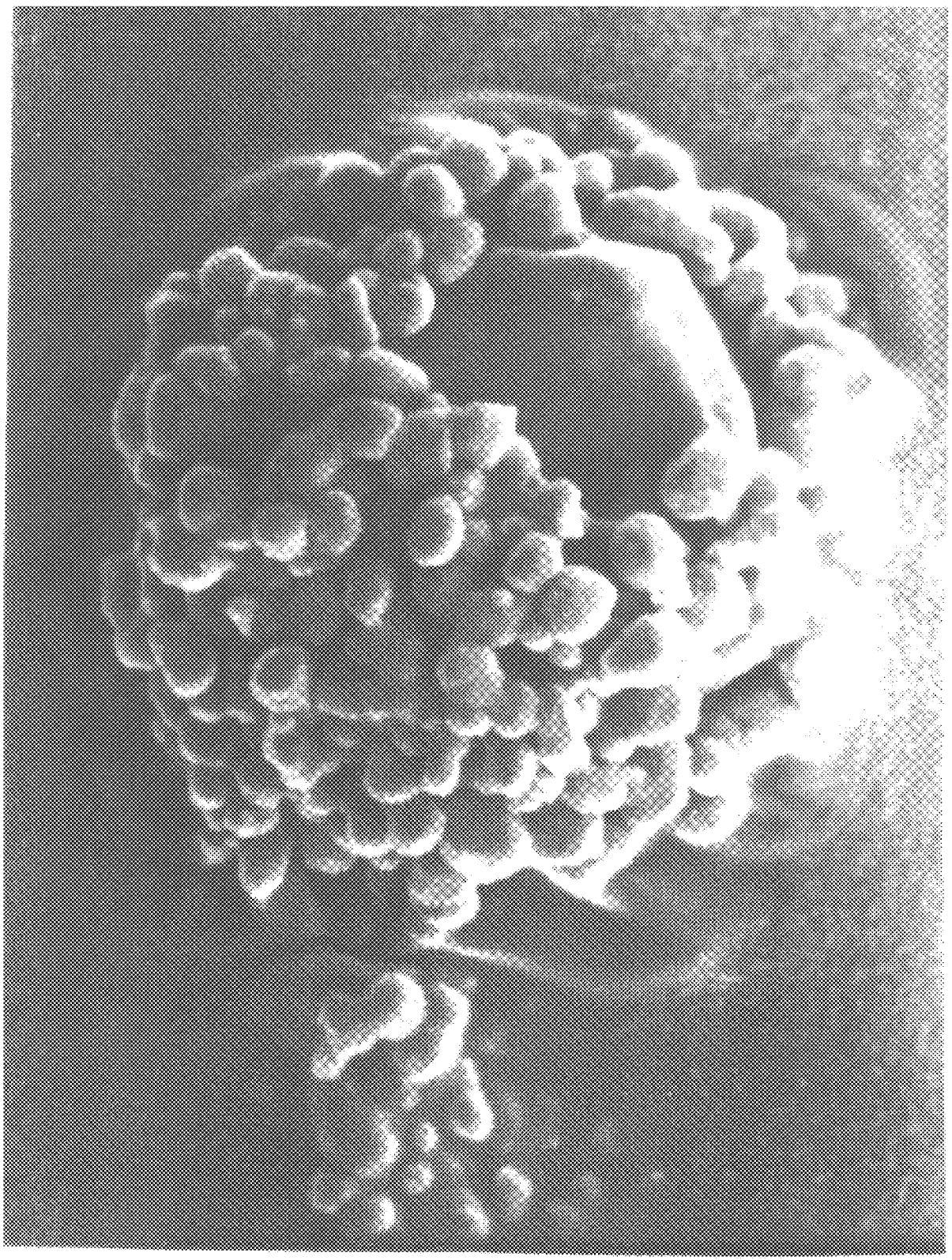
FIG. 1 is an enlarged (40,000×) photo of the spray-dried product and shows a single coated virus.

Microbial pesticides include the following organisms when they act as pesticides: 1) eucaryotic microorganisms including protozoa algae and fungi; 2) procaryotic microorganisms including bacteria and; 3) viruses. Biological pesticides which are particularly enhanced by the present invention are those that are degraded by UV light, thus, quickly losing their efficacy. Such UV light degradable pesticides include, but are not limited to, baculoviruses, granulosis viruses, *bacillus thuringensis,* Metarhizium spp. and Beauveria spp.

One embodiment of this invention pertains to many different viruses belonging to more than a dozen families that have been isolated from insects. Among those, members of the family Baculoviridae are considered to hold most promise for commercial insect control. More detailed information concerning the various aspects of baculoviruses as biopesticides can be found in the following publications: Ignoffo (968), Viruses-Living Insecticides, *Current Topics in Microbiology and immunology,* 42, 129–167; Arif and Jamieson (989), *The Baculoviruses, Biocontrol of Plant Diseases, Vol.* 1 (K. G. Mukerji & K. L. Garg, eds.); Blissard and Rohrmann (1990), Baculovirus Diversity and Molecular Biology, *Annual Review of Entomology* 35, 127–155; Adams and Bonami (1991), *Atlas of Invertebrate Viruses,* CRC Press, Boca Raton; Leisy and van Beek (1992), Baculoviruses, Possible Alternatives to Chemical Insecticides, *Chemistry & Industry,* Apr. 1992, pp. 250–254; Vlak (1993), Genetic engineering of baculoviruses for insect control in: "Molecular Approaches to Fundamental and Applied Entomology" (Oakeshott and Whitten, eds.), Springer Verlag, New York; WO 96/36712.

As pertains to the present invention, the term baculovirus embraces insecticides containing a nuclear polyhedrosis virus or granulosis virus. As will be appreciated, in relation to microbial insecticides, in general the microbial pathogens themselves, known as occlusion bodies, are not in practice isolated from the mediums in which they are prepared and processed but can be used in a heterogeneous mixture containing a range of materials from the nutrients to the host's metabolic waste products. Particularly preferred embodiments of this invention embrace insecticides containing, but not limited to, the nuclear polyhedrosis viruses and granulosis viruses for the bollworm (*Helicoverpa zea*), the cotton bollworm (*H. armigera*), the tobacco budworm (*Heliothis virescens*), the cabbage looper (*Trichoplusia ni*), the fall armyworm (*Spodoptera frugiperda*), the beet armyworm (*S. exigua*), the cotton leafworm (*S. littoralis*), the pink bollworm (*Pectinophora gossypiella*), the Douglas-fir tussock moth (*Orgyia pseudotsugata*), the spruce budworm (*Choristoneura fumiferana*), the western spruce budworm (*C. occidentalis*), the gypsy moth (*Lymantria dispar*), the European pine sawfly (*Neodiprion sertifer*) the diamondback moth (*Plutella xylostella*), the grapeleaf skeletonizer (*Harrisina americana*), the potato tuber worm (*Phthorimeaea operculella*), the black cutworm (*Agrotis ipsilon*), the codling moth (*Cydia pomonella*), the oriental fruit moth (*C. molesta*), and the navel orangeworm (*Amyelois transitella*).

Baculovirus production is known to those skilled in the art and occurs by fermentation in cultured insect cells (Vlak et. al., 1990, Bioreactor Development for Production of Viral Pesticides or Heterologous Proteins in "Insect Cell Cultures," *Ann. N.Y. Acad Sci.* 589, 399–418; Taticek et al., 1995, Overview of issues in bioreactor design and scale-up, in: "Baculovirus Expression Systems and Biopesticides," Shuler, Wood, Granados and Hammer, eds. Wiley-Liss, New York), or, in vivo in mass reared insect larvae (Ignoffo, 1967, Possibilities of Mass-Producing Insect Pathogens, *Internal. Colloq. Insect Pathol.* Netherlands, pp. 99–117; Shapiro 1986. In Vivo Production of Baculoviruses in: *The Biology of Baculoviruses*, Vol. II, CRC Press; Shieh 1989, Industrial production of viral pesticides, *Adv. Virus Res.* 36, 315–343).

Durable $TiO_2$ means $TiO_2$ (either anatase or rutile) that has been made durable by coating the $TiO_2$ particles with an oxide coating consisting of alumina, silica, or a combination of the two. An example of such a material is "TI-PURE®" Titanium Dioxide Pigment R-706 which is manufactured by the DuPont Company, Wilmington, Del. It is a $TiO_2$ on whose surface is deposited successive layers of silica and alumina which greatly reduces the photochemical reactivity of $TiO_2$. Any combination of silica or alumina or both may be contemplated however the preferred is one which has alumina as the outside layer. Preparation of these materials is described in Inorganic Pigments, Manufacturing Processes, Chemical Technology Review No. 166, M. H. Gutcho, ed. Noyes Data Corp. Park Ridge, N.J. 1980 and references cited therein. The important feature is that the alumina, silica, etc., should form a continuous, nonporous coating on the $TiO_2$ particles and not be present as a simple admixture. Typically these materials contain 1 to 4% silica (as $SiO_2$) and/or 4 to 9% alumina (as $Al_2O_3$), both based on the weight of $TiO_2$.

The durable $TiO_2$ can be simply mixed with the virus at a weight ratio of 10 to 90% weight/weight (w/w) $TiO_2$ to virus. Preferably though, the durable $TiO_2$ is substantially coated on the surface of the virus. Substantially coated means the $TiO_2$ is electrostatically fixed to the surface of the virus particle. Combination of the virus with the durable $TiO_2$ can occur by any standard means known in the art [*J. Econ. Entomol.* 69, 731(1976)] but is advantageously coated onto the individual virus particles by the process of the present invention. It is most preferred that the biological pesticide particles be completely coated as individual particles or as heteroflocculated particles (i.e., some interior particles may not be coated or are partially coated, but the outside of the heteroflocculated particles are completely coated).

According to one preferred embodiment of the present invention, addition of an aqueous slurry of the R-706 durable $TiO_2$ particles to a stirred aqueous slurry of a baculovirus at neutral pH (typically between about 5.5 and 8.0) causes the $TiO_2$ particles and the baculovirus solids to co-precipitate leaving a somewhat clear layer at the top of the liquid and a dense floc at the bottom. This is not observed with uncoated $TiO_2$ products (anatase or rutile) or $TiO_2$ products containing anionic surfaces such as silica-coated or those containing anionic surface-active agents. By virtue of its alumina coating, the durable $TiO_2$ particles are positively charged in aqueous suspension at neutral pH whereas the nuclear polyhedrosis virus, and by inference the other impurities in the baculovirus, are negative. The existing charge difference and mutual attraction causes the system to "collapse" and produces the observed flocculation. This is a very beneficial effect in that it results in the $TiO_2$ being electrostatically (as opposed to covalently) bound to the surface of the virus; thereby providing a very efficient means of surrounding each virus particle with a reversibly attachable UV shading material. This material is then spray dried to agglomerate the flocs into particles less than 50 micron mean volume diameter. This step provides resistance to redispersion of the durable $TiO_2$ away from the virus, which might occur during use in the presence of aggressive waters or surface active agents commonly employed in agricultural sprays, such as wetters or spreader-stickers while providing rapid dispersal under the very alkaline conditions of the target insect mid-gut where the pH can be $\geq 10.5$.

Certain particles which have light-filtering attributes but which bear a negative charge may be converted to bear a positive charge in which case the processes and benefits observed with durable $TiO_2$ are also observed. For example, a 5% suspension of Raven 430 Carbon (Columbian Chemicals Co.) containing 0.5% w/w of Ethoquad T/13-27W (Akzo Nobel Chemicals, Inc.) becomes positively charged. This suspension is also capable of flocculation like durable $TiO_2$ with the virus. Particles which have light filtering attributes include, but are not limited to $TiO_2$, carbon and zinc oxide. Any means for converting the particles to bear a positive charge is acceptable, however, coating the particles as described for durable $TiO_2$ and use of suitable quaternary ammonium surfactants are preferred such as Ethoquad.

In commercial operation, the present composition will usually, but not necessarily, be diluted in an aqueous matrix and sprayed on the locus to be treated.

The present composition can optionally include inert ingredients typically found in agricultural formulations such as mineral carriers or diluents, surfactants to enhance wetting of the spray target, vegetable flours, animal proteins or other gustatory stimulants to encourage feeding on the formulations, buffering agents to maintain an optimum pH for the formulation, antifoam agents, and preserving or stabilizing agents to inhibit microbial growth or other degradative processes.

The present composition can also contain up to about 50% w/w certain fluorescent brighteners or stilbenes; or, alternatively, be added separately to an aqueous spray solution of the present composition. These materials are well known to provide enhanced activity of a range of baculoviruses to their hosts and are active at concentrations typically ranging from 0.01 to 1% by weight of the spray liquid but useful at higher concentrations. Suitable stilbene materials are described in U.S. Pat. Nos. 5.124.149 and 5,246,936.

Preferred stilbene compounds are the analogs of 4,4'-diamino-2,2'-stilbene disulfonic acid, namely a Blancophor (available from Mobay Chemicals, Pittsburgh, Pa.) such as Blancophor BBH, Blancophor MBBH, Blancophor BHC, etc., a Calcifluor White (available from Sigma Chemical, St. Louis, Mo.) such as Calcifluor White. Calcifluor White M2R, Calcifluor White ABT, Calcifluor White LD, Calcifluor White RWP etc., a Leucophor (available from Sandoz Chemicals Corp., Charlotte, N.C.) such as Lucophor BS, Lucophor BSB, Lucophor EKB, Lucophor PAB, etc.; a Phorwite (available from Mobay Chemicals, Pittsburgh, Pa.) such as Phorwite AR, Phorwite BBU, Phorwite BKL, Phorwite CL, Phorwite RKK, etc., Blancophor BBH, Calcifluor White M2R, and Phorwite AR are the most preferred stilbene compounds.

EXAMPLE 1

This example illustrates the general procedure for producing the flocculated durable $TiO_2$/virus mixtures. One hundred grams of durable $TiO_2$ particles (DuPont TI-PURE® Grade R-706) was bead-milled for 20 min with 100 g of deionized water. The pH was adjusted during milling to a range of 7.0 to 8.0 with dropwise addition of sodium hydroxide. The resultant particle size of this positively charged suspension was 0.8 microns mvd (mean volume diameter). This slurry was added with high speed mixing to 500 g of virus [*Autographa californica* multicapsid nuclear polyhedrosis virus (MNPV)] aqueous slurry (15% w/w suspended solids) obtained by infection of *Heliothis virescens* larvae. The slurry had been de-oiled by centrifugation. The virus solids typically contain $1 \times 10^{10}$ to $1 \times 10^{11}$ virus occlusion bodies OBs per gram, the virus used in this example contained $2.4 \times 10^{10}$ (OBs) per gram dry weight. The pH of the resulting slurry was lowered to 6.5 by dropwise addition of hydrochloric acid and stirred briefly to permit completion of the process. The resultant mixture was spray dried in a pilot-scale spray dryer at an inlet temperature of 185° C. and an outlet temperature of 60 to 65° C. A total of 100 g of durable $TiO_2$ coated virus formulation was recovered nominally containing 42% ($1 \times 10^{10}$ virus OBs per gram). The virus concentration cannot be directly measured in these systems because release from the matrix is only achieved at pH levels high enough to begin dissolving the virus particles. The particle size of the spray-dried material was 20.2 microns mvd and an example of a single coated virus is shown in FIG. 1.

EXAMPLE 2

This example illustrates the general procedure for preparing a mixture as in Example 1 with a different virus and the addition of a fluorescent brightener. Fifty grams of durable $TiO_2$ particles (DuPont TI-PURE® Grade R-706) and 25.2 g of a stilbene brightener (Blankophor BBH) were bead-milled for 20 min with 75 g of deionized water. The pH was adjusted during milling to a range of 7.0 to 8.0 with dropwise addition of sodium hydroxide. The resultant particle size was 1.1 microns mvd. This slurry was added with high speed mixing to 547 g of virus (*Helicoverpa zea SNPV*) aqueous slurry (20% w/w suspended solids). The virus solids typically contain $1 \times 10^{10}$ to $1 \times 10^{11}$ virus OBs per gram, the virus used in this example contained $5.9 \times 10^{10}$ OBs per gram dry weight. The pH of the resultant slurry was lowered to 6.5 by dropwise addition of hydrochloric acid. The resultant mixture was dried in the same spray dryer as in Example 1 at an inlet temperature of 185° C. and an outlet temperature of 60 to 65° C. The durable $TiO_2$ coated virus material was calculated to contain $5.3 \times 10^9$ OBs per gram. The particle size of the spray-dried material was 18.9 microns mvd.

EXAMPLE 3

This example illustrates the general procedure for preparing a mixture as in Example 1 with a different virus and the addition of a feeding stimulant. Thirty-five grams of durable $TiO_2$ particles (DuPont TI-PURE® Grade R-706) and 65 g of corn flour were bead-milled for 20 min with 516 g of deionized water. The pH was adjusted during milling to a range of 7.0 to 8.0 with dropwise addition of sodium hydroxide. The resultant particle size was 2.2 microns mvd. This slurry was added with high speed mixing to an aqueous slurry of 500 g of the virus of Example 1 (*Autographa californica* MNPV) slurry (25% w/w suspended solids). The virus solids typically contain $1 \times 10^{10}$ to $1 \times 10^{11}$ OBs per gram, the virus used in this example contained $2.4 \times 10^{10}$ OBs per gram dry weight. The pH of the resultant slurry was lowered to 6.5 by dropwise addition of hydrochloric acid. The resultant mixture was dried in a spray dryer as in Example 1. The durable $TiO_2$ coated material was calculated to contain $1.3 \times 10^{10}$ virus OBs per gram. The particle size of the spray-dried material was 26.8 microns mvd.

EXAMPLE 4

This example illustrates the general procedure for preparing a mixture as in Example 1 with a different virus and the addition of a binder. Twenty-five grams of durable $TiO_2$ particles (DuPont TI-PURE® Grade R-706) and 10 g of corn starch were bead-milled for 20 min with 75 g of deionized water. The pH was adjusted during milling to a range of 7.0 to 8.0 with dropwise addition of sodium hydroxide. This slurry was added with high speed mixing to 200 g of an aqueous slurry of virus (*Autographa californica* MNPV) slurry (20% w/w suspended solids). The virus solids typically contain $1 \times 10^{10}$ to $1 \times 10^{11}$ OBs per gram, the virus used in this example contained $2.4 \times 10^{10}$ OBs per gram dry weight. The pH of the resultant slurry was lowered to 6.5 by dropwise addition of hydrochloric acid. The resultant mixture was spray dried in a spray dryer as in Example 1. The durable $TiO_2$ coated material was calculated to contain $1.3 \times 10^{10}$ virus OBs per gram.

EXAMPLE 5

This example illustrates the field stability achieved using the materials and process indicated in Example 1. Plots consisted of two 100 ft rows divided into four 25 ft replicates. Treatments were applied at 20 gallons-per-acre (0.18 $m^3$ per hectare) with a 0.125% w/w aqueous suspension of unformulated virus (*Autographa californica* MNPV) using an application rate of $2.5 \times 10^{11}$ OBs per acre ($1 \times 10^{10}$ OBs per gram of virus). Another row of cotton was treated in the same manner and occlusion body rate using a 0.66% w/w aqueous dispersion of the powder described in. Example 1. At various time intervals whole cotton leaf samples were taken from each treated row along with an uncontaminated check row. Following application, plants were allowed to dry then 16 leaves per replicate was excised for laboratory bioassay. A single leaf was placed into each cell of a 16 celled jelly tray. A single 3-day-old *H. virescens* larva was also added to each cell. Test units were held at 28° C. in 14 h of light for a total of 5 days. Mortality was assessed on the fifth day. Repeated leaf collections and bioassays were conducted 1, 2, and 4 d following the application. The results shown in Table 1 illustrate the stabilization achieved on addition of the durable $TiO_2$ particles.

TABLE 1

Comparison of formulated virus and unformulated virus

| | Percent Kill | |
|---|---|---|
| Sampling Time | Unformulated | Formulation in Example 1 |
| 0 | 58 | 49 |
| 1 day | 30 | 72 |
| 2 days | 16 | 56 |
| 4 days | 6 | 47 |

EXAMPLE 6

This example compares the activity of formulations prepared as in Examples 1 and 3 (with and without spray drying) as well as showing that the activity differences are maintained on a different surface (glass) as well as addition of a commonly used agricultural surfactant Tween 20®. In this Example, microscope slide coverslips were treated with 10 μl of virus preparation containing $1 \times 10^8$ OBs per ml as calculated from the amount contained in each preparation and the suspension also contained 0.2% w/w Tween-20® surfactant. Half of the treated coverslips were exposed to natural mid-day sunlight for 4 h and the other half kept in darkness. The virus was stripped from each of the coverslips by sonication (10 s) in 10 ml of distilled water. A molten lepidopteran diet was added to the suspension of each sample and then cast into 2-25 well bioassay trays. Each replicate consisted of fifty 3-day-old *H. virescens* larvae. Mortality assessments were made 144 h post exposure. The percent activity remaining was calculated by comparing UV exposed to UV unexposed virus. This example also illustrates the importance of spray drying the product prior to use.

TABLE 2

Comparison of formulations prepared according to Examples 1 and 3 after 4 hours of sun exposure.

| Percent Kill | | |
|---|---|---|
| Example 1 | Example 3 | Example 1 w/o Spray Drying |
| 82 | 96 | 17 |

What is claimed is:

1. A pesticidal composition comprising negatively changed particles of a viral pesticide and positively charged particles of durable TiO2 in an amount sufficient to substantially coat the particles of the viral pesticide wherein said durable $TiO_2$ particles have a continuous, nonporous coating comprising alumina forming a cationic surface on said durable $TiO_2$ particles, and wherein said durable $TiO_2$ particles are electrostatically fixed to the surface of the particles of said viral pesticide.

2. The pesticidal composition of claim 1 wherein the viral pesticide is a baculovirus.

3. The pesticidal composition of claim 2 wherein the baculovirus contains genes encoding an insecticidal protein.

4. The pesticide composition of claim 2 wherein the particles of baculovirus substantially coated with durable $TiO_2$ have a mean particle size distribution of less than about 50 μm.

5. The pesticidal composition of claim 1 further comprising at least one of a surfactant, a solid diluent or a liquid diluent.

6. The pesticidal composition of claim 5 further comprising a fluorescent brightener.

7. A process for preparing the composition of claim 1 comprising mixing positively charged durable $TiO_2$ particles having a continuous, nonporous coating comprising alumina forming a cationic surface on said durable $TiO_2$ particles with an aqueous slurry comprising negatively charged viral pesticide particles wherein the pH of the aqueous slurry ranges from 5.5 to 8, and wherein said durable $TiO_2$ particles are electrostatically affixed to the surface on the particles of said viral pesticide as a result of mixing said durable $TiO_2$ particles with said aqueous slurry of viral pesticide particles at said pH range, and spray drying the resulting mixture.

8. A method of controlling agricultural pests comprising: applying to the pests or their environment a pesticidally effective amount of the pesticidal composition of claim 1.

* * * * *